(12) United States Patent
Aldrich et al.

(10) Patent No.: US 10,988,506 B2
(45) Date of Patent: *Apr. 27, 2021

(54) CYCLIC TETRAPEPTIDE STEREOISOMERS (71) Applicant: University of Kansas, Lawrence, KS (US)

(72) Inventors: Jane V. Aldrich, Lawrence, KS (US); S P Sanjeewa Nilendra Senadheera, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/383,016

(22) Filed: Apr. 12, 2019

(65) Prior Publication Data

US 2019/0241612 A1 Aug. 8, 2019

Related U.S. Application Data

(63) Continuation of application No. 15/325,177, filed as application No. PCT/US2015/040184 on Jul. 13, 2015, now Pat. No. 10,259,843.

(60) Provisional application No. 62/023,392, filed on Jul. 11, 2014.

(51) Int. Cl.
  *C07K 5/12* (2006.01)
  *A61K 38/00* (2006.01)

(52) U.S. Cl.
  CPC ............ *C07K 5/126* (2013.01); *C07K 5/12* (2013.01); *A61K 38/00* (2013.01)

(58) Field of Classification Search
  None
  See application file for complete search history.

(56) References Cited

U.S. PATENT DOCUMENTS

| 5,885,959 | A | 3/1999 | Hirai et al. |
| 8,809,278 | B2 | 8/2014 | Aldrich et al. |
| 10,259,843 | B2 * | 4/2019 | Aldrich ............... C07K 5/12 |
| 2009/0214650 | A1 | 8/2009 | Ehrich |

FOREIGN PATENT DOCUMENTS

WO   WO 2010/006267   * 1/2010

OTHER PUBLICATIONS

Extended European Search Report for EP 19168888.6, dated Jun. 19, 2019, 13 pages.
"Poster Abstracts ED—Quinn, John P", Neuropeptides, Churchill Livingstone, GB, vol. 43 No. 5, Oct. 1, 2009, pp. 401-455.
Beardsley, et al. "Differential effects of the novel kappa opioid receptor antagonist, JDTic, on reinstatement of cocaine-seeking induced by footshock stressors vs cocaine primes and its antidepressant-like effects in rats", Psychopharmacology, Springer, Berlin, DE, vol. 183, No. 1, Nov. 1, 2005, pp. 118-126.
Reddy, P.A., et al; "An Improved Synthetic Approach to Head-to-Tail Cyclic Tetrapeptides", Proceedings of the 23rd American Peptide Symposium, American Peptide Society, 2013, 2 pages.
International Search Report and Written Opinion for PCT/US2015/040184 dated Jul. 13, 2015.
Aldrich, J.V., et al; "Alanine analogues of [D-Trp]CJ-15, 208: novel opioid activity profiles and prevention of drug- and stress-induced reinstatement of cocaine-seeking behaviour: Opioid profiles of [D-Trp]CJ-15,208 Ala analogues"; British Journal of Pharmacology, vol. 171, No. 13; Jun. 10, 2014, pp. 3212-3222.
Dolle, R.E., et al; "Nascent structure-activity relationship study of a diastereomeric series of kappa opioid receptor antagonists derived from CJ-15,208"; Bioorganic & Medicinal Chemistry Letters, Pergamon, Amsterdam, NL; vol. 19, No. 13, Jul. 1, 2009, pp. 3647-3650.
Shainnel, O Eans, et al.; "The macrocyclic tetrapetide [D=Trp]CJ-15,208 produces short-acting [kappa] opioid receptor antagonism in the CNS after oral administration: Orally active peptide antagonizes KOR in CNS"; British Journal of Pharmacology, vol. 169, No. 2, Apr. 25, 2013; pp. 426-436.
Extended European Search Report received in EP Serial No. 15818825.0, dated Feb. 16, 2018, 10 pages.
U.S. Appl. No. 15/325,177, Feb. 2, 2018, Office Action.
U.S. Appl. No. 15/325,177, Nov. 29, 2018, Notice of Allowance.

* cited by examiner

*Primary Examiner* — Sergio Coffa
(74) *Attorney, Agent, or Firm* — Ray Quinney & Nebeker P.C.; Paul N. Taylor (57) ABSTRACT

Cyclic tetrapeptide stereochemical isomers of CJ-15,208, pharmaceutical compositions from such cyclic tetrapeptides, and methods of using such pharmaceutical compositions. The cyclic tetrapeptide compounds and pharmaceutical compositions disclosed herein are potent analgesics active in several pain models with generally minimal tolerance and reduced likelihood to induce addiction relative to other known opiates.

15 Claims, 5 Drawing Sheets
Specification includes a Sequence Listing.

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: The following sequence is for a cyclic
      tetrapeptide.

<400> SEQUENCE: 1

Phe Pro Phe Trp
1

CYCLIC TETRAPEPTIDE STEREOISOMERS

CROSS REFERENCE TO RELATED APPLICATIONS

The application is a continuation of U.S. patent application Ser. No. 15/325,177, filed Jan. 10, 2017, which is a U.S. Nationalization of PCT Application No. PCT/US2015/040184, filed on Jul. 13, 2015, which claims the benefit of and priority to U.S. Prov. App. Ser. No. 62/023,392 filed 11 Jul. 2014, the entireties of which are incorporated herein by reference in their entireties.

GOVERNMENT RIGHTS

This invention was made with government support under Grant Numbers R01 DA018832 and R01 DA023924 awarded by the National Institute of Health. The government has certain rights in this invention."

BACKGROUND

Opioid receptors are a group of inhibitory G protein-coupled receptors with opioids as ligands. Opioid receptors are distributed widely in the brain, and are found in the spinal cord and digestive tract. The types of opioid receptors are mu (μ) MOR, kappa (κ) KOR, and delta (δ) DOR. The receptors were generally named using the first letter of the first ligand that was found to bind to them. For instance, morphine was the first chemical shown to bind to mu receptors. The first letter of the drug morphine is m, rendered as the corresponding Greek letter μ. In similar manner, a drug known as ketocyclazocine was first shown to interact with kappa receptors, while the delta receptor was named after the mouse vas deferens tissue in which the receptor was first characterized. The mu receptor is the primary target of currently used narcotic analgesics.

The opioid receptor types are ~70% identical with substantial differences located at N and C termini as well as other regions of the receptors. It is thought that the G protein binds to the third intracellular loop of the opioid receptors. Both in mice and humans, the genes for the various receptor subtypes are located on different chromosomes.

Some characteristics of the MOR, KOR, and DOR are presented below.

The mu (μ) opioid receptor (MOR) is found in the brain (e.g., in the cortex (laminae III and IV), thalamus, striosomes, periaqueductal gray, and rostral ventromedial medulla), in the spinal cord (e.g., in the substantia gelatinosa), in the peripheral sensory neurons, and in the intestinal tract. The mu receptor has roles in analgesia, physical dependence, respiratory depression, miosis, euphoria, reduced gastrointestinal motility, physical dependence, and possible vasodilation.

The kappa (κ) opioid receptor (KOR) is found in the brain (e.g., in the hypothalamus, periaqueductal gray, and claustrum), in the spinal cord (e.g., in the substantia gelatinosa) and in the peripheral sensory neurons. Kappa opioid receptors play a role in analgesia, anticonvulsant effects, depression, dissociative/hallucinogenic effects, diuresis, dysphoria, miosis, neuroprotection, sedation, and stress.

The delta (δ) opioid receptor (DOR) is found in the brain (e.g., in the pontine nuclei, amygdala, olfactory bulbs, deep cortex) and in the peripheral sensory neurons. Delta opioid receptors play a role in analgesia, antidepressant effects, convulsant effects, physical dependence, and may modulate μ-opioid receptor-mediated respiratory depression The macrocyclic peptide CJ-15,208 (cyclo[Phe-D-Pro-Phe-Trp] (SEQ ID NO. 1) exhibits mixed opioid agonist/kappa opioid receptor (KOR) antagonist activity in vivo and is a promising lead compound for developing novel therapeutics for the treatment of pain and drug abuse. We synthesized analogs of this lead peptide to explore the influence of the aromatic residues on the analogs' opioid activity profiles.

SUMMARY

Disclosed herein are cyclic tetrapeptide compounds, pharmaceutical compositions, and methods of using such pharmaceutical compositions. The cyclic tetrapeptide compounds and pharmaceutical compositions disclosed herein are potent analgesics active in several pain models with, in some cases, decreased tolerance and reduced likelihood to induce addiction relative to other known opiates.

In an embodiment, a cyclic tetrapeptide having a sequence of cyclo[Phe-Pro-Phe-Trp] (SEQ ID NO. 1) having a structure of Formula 1 or a derivative thereof is disclosed.

Formula 1

In the illustrated structure of Formula 1, the wavy lines in the amino acid sidechains indicate the existence of an undefined stereocenter. Each of these amino acid stereocenters can be defined as 'D' or 'L' using the standard notation for amino acids. Accordingly, the cyclic tetrapeptide of Formula 1 may have an amino acid configuration of one of LDDL, DDLL, DDDL, DDLD, LDDD, LLLL, DDDD, LLDL, DLLL, DLDL, LLLD, LLDD, DLDD, or DLLD. A cyclic tetrapeptide having an amino acid configuration of LDLL is specifically excluded from the claims herein. The naturally occurring cyclic tetrapeptide CJ-15,208 has the amino acid configuration of LDLL.

Preferably, the cyclic tetrapeptide of Formula 1 has an amino acid configuration of one of DDLL, DDDL, LDDD, DDLD, or DDDD. More preferably, the cyclic tetrapeptide of Formula 1 has an amino acid configuration of one of DDLL, DDDL, LDDD or DDDD. Most preferably, the cyclic tetrapeptide of Formula 1 has an amino acid configuration of DDDL or DDDD.

In another embodiment, a pharmaceutical composition is disclosed. The pharmaceutical composition includes a pharmaceutically acceptable excipient or carrier, and a therapeutically effective amount of the cyclic tetrapeptide of Formula I having an amino acid configuration of one of LDDL, DDLL, DDDL, DDLD, LDDD, LLLL, DDDD, LLDL, DLLL, DLDL, LLLD, LLDD, DLDD, or DLLD. Preferably, the cyclic tetrapeptide of Formula 1 has an amino acid configuration of one of DDLL, DDDL, LDDD, DDLD, or DDDD. More preferably, the cyclic tetrapeptide of Formula 1 has an amino acid configuration of one of DDLL, DDDL, LDDD or DDDD. Most preferably, the cyclic tetrapeptide of Formula 1 has an amino acid configuration of DDDL or DDDD.

In another embodiment, a method for treating pain is disclosed. The method includes administering to a subject a therapeutically effective amount of a pharmaceutical composition containing a cyclic tetrapeptide of Formula I having an amino acid configuration of one of LDDL, DDLL, DDDL, DDLD, LDDD, LLLL, DDDD, LLDL, DLLL, DLDL, LLLD, LLDD, DLDD, or DLLD. Preferably, the cyclic tetrapeptide of Formula 1 has an amino acid configuration of one of DDLL, DDDL, LDDD, DDLD, or DDDD. More preferably, the cyclic tetrapeptide of Formula 1 has an amino acid configuration of one of DDLL, DDDL, LDDD or DDDD. Most preferably, the cyclic tetrapeptide of Formula 1 has an amino acid configuration of DDDL or DDDD.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

Disclosed herein are cyclic tetrapeptide compounds, pharmaceutical compositions, and methods of using such pharmaceutical compositions. The cyclic tetrapeptide compounds and pharmaceutical compositions disclosed herein are potent analgesics active in several pain models with generally decreased tolerance and reduced likelihood to induce addiction relative to other known opiates.

Recently, it has been shown that a cyclic tetrapeptide, CJ-15,208 and having Formula 1, can interact with opioid receptors (U.S. Pat. No. 5,885,959). CJ-15,208 (i.e., cyclo[Phe-D-Pro-Phe-Trp]) (SEQ ID NO. 1) appears to be the natural product (see, Ross et al., Tetrahedron Letters, 2010, 51, 5020-5023). The interaction was indicated to provide analgesic activity, which can be attributed to being an agonist, and provide detoxification activity, which can be attributed to being an antagonist. Accordingly, the true functionality of CJ-15,208 was not properly characterized. It has now been found that CJ-15,208 has weak antagonist and agonist activities at kappa opioid receptors (KOR) in vivo. The structure of CJ-15,208 is shown below.

CJ-15,208 (cyclo[Phe-D-Pro-Phe-Trp])

It has now been found that cyclic tetrapeptides that are stereochemical isomers of CJ-15,208 can have superior opioid receptor agonist activity (i.e., pain relieving activity), and thereby can be useful as analgesics for the treatment of inflammatory and neuropathic pain. It has further been found that that selected cyclic tetrapeptides disclosed herein show decreased tolerance and reduced likelihood to induce addiction relative to other known opiates.

The cyclic tetrapeptides discussed herein have a structure of Formula 1 or a derivative thereof.

Formula 1

In the illustrated structure of Formula I, the wavy lines in the amino acid sidechains indicate the existence of an undefined stereocenter. Each of these stereocenters can be defined as 'D' or 'L' according to standard amino acid convention. Accordingly, the cyclic tetrapeptide of Formula I may have an amino acid configuration of one of LDDL, DDLL, DDDL, DDLD, LDDD, LLLL, DDDD, LLDL, DLLL, DLDL, LLLD, LLDD, DLDD, or DLLD. Discussions of analogs or derivatives herein expressly exclude CJ-15,208, which has an amino acid configuration of LDLL.

As used herein, "derivatives" are considered to include R changes to the amino acid side chains of amino acids of the cyclic tetrapeptide of Formula 1. Derivatives are considered to include atom or substituent exchanges such as one or more hydrogen atoms being substituted with an alkyl, halogen, hydroxy, amine, combinations thereof, or the like. For instance, a number of phenylalanine (Phe) and tryptophan (Trp) derivatives are known in the art. Accordingly, Phe and Trp derivatives may include, but are not limited to, changes where one or more hydrogen, carbon or hetero atoms of the side chain are replaced with one or more of halo, amino, straight-chain alkyl, branched alkyl, alkoxy, nitro, halo alkyl, cyano, or hydroxy.

The cyclic tetrapeptides disclosed and claimed herein are completely different in structure from known opioid ligands, which are typically either peptide or nonpeptide. For instance, the cyclic tetrapeptides lack a free N-terminal basic amine found in endogenous opioid peptide ligands and other peptides with high affinity for opioid receptors. Interestingly, changing the stereochemistry of the Trp residue, which is believed to be important for KOR binding, results in a new analog which retains KOR affinity comparable to the parent CJ-15,208, which is surprising and unexpected. In both CJ-15,208 and the D-Trp analog of CJ-15,208 (cyclo[Phe-D-Pro-Phe-D-Trp] (SEQ ID NO. 1) (Formula 2802)). In U.S. Pat. No. 8,809,278 it was shown that substitution of Phe by Ala enhances affinity of the cyclic tetrapeptide for KOR by about 4- to 10-fold. In contrast to linear peptides, the cyclic tetrapeptides are metabolically stable to proteases and exhibit enhanced membrane penetration (e.g. through the blood-brain barrier).

The cyclic tetrapeptides shown below in Tables 1 and 2 can be used as analgesics for the treatment of pain. In addition, these cyclic tetrapeptides, which are opioid receptor ligands, can be used in the prevention, inhibition, and/or treatment of drug abuse, specifically to treat, inhibit, and/or prevent stress-induced drug seeking behavior. Cyclic tetrapeptides can be metabolically stable, and can be active following systemic (e.g., oral (per os), subcutaneous, s.c., intravenous, i.v., or the like) administration. The cyclic tetrapeptide antagonists can block stress-induced reinstatement of drug-seeking behavior following systemic administration.

In one embodiment, the cyclic tetrapeptides disclosed and claimed herein can be used as analgesics. Opioid receptor agonists are drug compounds that activate opioid receptors. Full agonist opioids activate the opioid receptors fully resulting in the full opioid effect. Examples of full agonists are heroin, oxycodone, methadone, hydrocodone, morphine, opium and others. The tetrapeptides disclosed and claimed are demonstrated herein to have analgesic properties similar to traditional opioids. As such, the cyclic tetrapeptides disclosed and claimed herein can be used to treat and/or inhibit pain treatable by an analgesic.

The functionality of cyclic tetrapeptides was studied by preparing stereochemical isomers of CJ-15,208, and testing the interactions with opioid receptors in vitro and in various pain models in vivo. It has now been found that stereochemical changes to the amino acids in the cyclic tetrapeptide actually increased analgesic effects in relevant pain assays in a surprising and unexpected manner.

Figure 5:
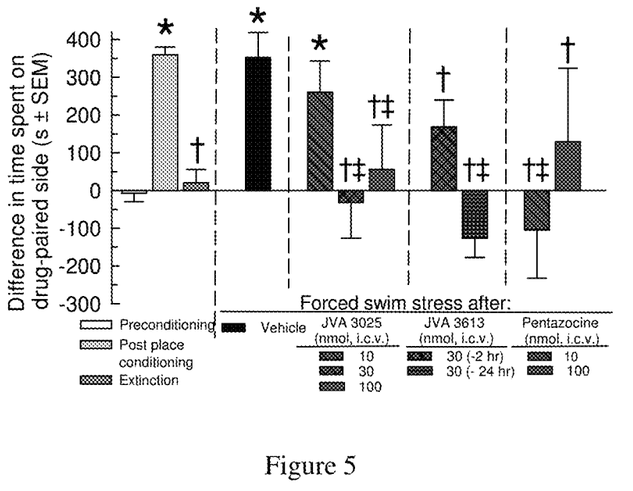
FIG. 5 illustrates that administration of selected cyclic tetrapeptides prevents stress-induced reinstatement of cocaine seeking behavior.

Because opioid receptor ligands are known to have central nervous system effects, the cyclic tetrapeptides disclosed and claimed herein can also be used for the treatment of drug abuse by blocking stress-induced reinstatement of drug-seeking behavior following systemic administration (see, e.g., FIG. 5). Drugs included in this are at least cocaine, alcohol, methamphetamines, amphetamines, opioids (e.g., narcotic opioid alkaloids, morphine, codeine, heroin, oxycodone, hydrocodone, and any benzylisoquinoline alkaloid; synthetic opiates, fentanyl, meperidine and methadone), and the like. Accordingly, the cyclic tetrapeptides could be used as a prophylactic to prevent relapse to drug addiction. It is expected that the cyclic tetrapeptides may also be active in models for treatment of drugs of abuse other than cocaine, specifically opiates and amphetamine, and possibly others (e.g., alcohol and nicotine).

Likewise, in one embodiment, the cyclic tetrapeptides disclosed herein may be able to be used to treat, inhibit, and/or prevent depression. Based on the activity of small molecule opioid receptor ligands, the cyclic tetrapeptides are expected to exhibit antidepressant activity. Similarly, the cyclic tetrapeptides can be used for treating, inhibiting, and/or preventing anxiety.

Structures of Stereochemical Isomers of CJ-15,208

TABLE 1

| JVA # | Compound | Structure |
|---|---|---|
| 2801 (LDLL)* | cyclo[Phe-D-Pro-Phe-Trp] (SEQ ID NO: 1) | |

TABLE 1-continued

| JVA # | Compound | Structure |
|---|---|---|
| 2802 (LDLD) | cyclo[Phe-D-Pro-Phe-D-Trp] (SEQ ID NO: 1) | |
| 3606 (LDDL) | cyclo[Phe-D-Pro-D-Phe-Trp] (SEQ ID NO: 1) | |
| 3605 (DDLL) | cyclo[D-Phe-D-Pro-Phe-Trp] (SEQ ID NO: 1) | |
| 3607 (DDDL) | cyclo[D-Phe-D-Pro-D-Phe-Trp] (SEQ ID NO: 1) | |

TABLE 1-continued

| JVA # | Compound | Structure |
|---|---|---|
| 3609 (DDLD) | cyclo[D-Phe-D-Pro-Phe-D-Trp] (SEQ ID NO: 1) | |
| 3608 (LDDD) | cyclo[Phe-D-Pro-D-Phe-D-Trp] (SEQ ID NO: 1) | |
| 3612 (LLLL, all L) | cyclo[Phe-Pro-Phe-Trp] (SEQ ID NO: 1) | |

TABLE 1-continued

| JVA # | Compound | Structure |
| --- | --- | --- |
| 3613 (DDDD, all D) | cyclo[D-Phe-D-Pro-D-Phe-D-Trp] (SEQ ID NO: 1) | |
| 3614 (DLDD) | cclo[D-Phe-Pro-D-Phe-D-Trp] (SEQ ID NO: 1) | |

TABLE 2

| JVA # | Compound | Structure |
| --- | --- | --- |
| 3636 (LLDL) | cyclo[Phe-Pro-D-Phe-Trp] (SEQ ID NO: 1) | |

TABLE 2-continued

| JVA # | Compound | Structure |
|---|---|---|
| 3637 (DLLL) | cyclo[D-Phe-Pro-Phe-Trp] (SEQ ID NO: 1) | |
| 3638 (DLDL) | cyclo[D-Phe-Pro-D-Phe-Trp] (SEQ ID NO: 1) | |
| 3639 (LLLD) | cyclo[Phe-Pro-Phe-D-Trp] (SEQ ID NO: 1) | |
| 3640 (LLDD) | cyclo[Phe-Pro-D-Phe-D-Trp] (SEQ ID NO: 1) | |

TABLE 2-continued

| JVA # | Compound | Structure |
|---|---|---|
| 3641 (DLLD) | cyclo[D-Phe-Pro-Phe-D-Trp] (SEQ ID NO: 1) | |

*The shorthand notation in parantheses indicates the amino acid configurations within the peptide The cyclic peptide stereochemical isomers of CJ-15,208 disclosed herein and shown in Table 1 were synthesized by a combination of solid phase synthesis with cyclization in solution.

The peptides of Table 1 shown below in Tables 3 and 4 were evaluated in radioligand binding assays for mu, kappa and delta opioid receptor affinities in vitro, and in the mouse 55° C. warm water tail withdrawal assay in vivo for antinociception and opioid antagonist activity. Additionally, peptides 3605, 3607, and 3608 showed significant analgesic properties when evaluated in other pain models (FIGS. 1-3B), and peptides 3605 and 3607 showed no evidence of inducing drug seeking behavior when evaluated in a conditioned place response assay (FIG. 4).

In Vitro Receptor Binding Affinities[a]

TABLE 3

| JVA # | KOR | $K_i$ (nM ± SEM)[b] MOR | DOR[c] | Selectivity KOR/MOR/ DOR |
|---|---|---|---|---|
| 2801 (CJ-15,208) | 35.4 ± 3.6 (4) 16.9 ± 5.2 (3) | 619 ± 87 (3) 200 ± 54 (2) | 1720 ± 350 (5) | 1/18/49 1/12/102 |
| 3605 | 5120 ± 690 | >10,000 (4) | >10,000 | |
| 3606 | 362 ± 51 | 3920 ± 200 (3) | >10,000 | 1/11/>27 |
| 3607 | 2560 ± 480 | 7780 ± 410 | >10,000 | 1/3/>3.8 |
| 2802 ([D-Trp]CJ-15,208) | 30.6 ± 3.4 (5) 7.0 ± 4.8 (3) | 259 ± 29 | 4190 ± 860 (6) | 1/8.5/137 1/37/599 |
| 3609 | >10,000 | >10,000 | >10,000 | — |
| 3608 | 353 ± 19 | 5800 ± 1450 | >10,000 | 1/16/>28 |
| 3613 | 2010 ± 270 | >10,000 | >10,000 | 1/>4.9/4.9 |

[a]None of these compounds exhibit agonist activity at KOR or MOR in the GTPγS assay at 10 µM.

The cyclic tetrapeptide stereoisomers of CJ-15,208 have relatively low affinity for KOR, MOR, and DOR. Only two stereoisomers, 3606 and 3608, exhibit $K_i$<1 µM and these stereoisomers show very low affinity for MOR ($K_i$>1 µM) and negligible affinity for DOR. None of these stereoisomers exhibit evidence of agonist activity in the in vitro functional assay.

Nonetheless, the analogs generally exhibited potent antinociception in vivo comparable to CJ-15,208 following both intracerebroventricular (i.c.v.) and oral (per os) administration in spite of reductions in opioid receptor affinities in vitro (Table 4).

Antinociceptive and Opioid Antagonist Activity:

TABLE 4

| | $ED_{50}$ (95% CI) | | | |
|---|---|---|---|---|
| JVA # | i.c.v. (nmol) | p.o. (mg/kg) | Receptors involved | Antagonism (dose, nmol) |
| 2801 (CJ-15,208) | 1.74 (0.62-4.82) | 3.49 (1.98-5.73) | KOR, MOR | KOR |
| 3605 | 0.75 (0.36-1.44) | 7.62 (5.12-12.2) | KOR, MOR, DOR | KOR (30), DOR (100) |
| 3606 | Partial agonist (~60% max) | >30 (~45% response @ 30 mg/kg) | KOR, MOR | None (100) |

TABLE 4-continued

| | $ED_{50}$ (95% CI) | | | |
|---|---|---|---|---|
| JVA # | i.c.v. (nmol) | p.o. (mg/kg) | Receptors involved | Antagonism (dose, nmol) |
| 3607 | 1.00 (0.64-1.60) | 4.12 (3.30-5.31) | KOR, DOR (not MOR) | None (30) |
| 2802 ([D-Trp]CJ-15,208) | ~40% @ 30 nmol | ~25% @ 60 mg/kg | KOR | KOR |

TABLE 4-continued

|  | $ED_{50}$ (95% CI) | | | |
|---|---|---|---|---|
| JVA # | i.c.v. (nmol) | p.o. (mg/kg) | Receptors involved | Antagonism (dose, nmol) |
| 3609 | 2.39 (1.40-4.56) | ≥10 mg/kg (~60% at 30 mg/kg) | DOR, KOR (not MOR) | None (30) |
| 3608 | 0.56 (0.38-0.91) | 4.72 (3.70-6.39) | KOR, MOR, DOR | DOR (100) |
| 3613 | 0.51 (0.39-0.67) | 2.47 (0.97-4.71) | DOR, MOR (not KOR) | DOR (30) |

All of these stereoisomers of 2801 and 2802 except 3606 are potent full agonists in the antinociception assay after central administration. All of these stereoisomers except 3606 and 3609 are potent full agonists after oral administration. Interestingly, these in vivo results do not correlate with the in vitro results. This indicates that the mechanism(s) of opioid receptor agonism in vivo may be complex.

The evidence showed that multiple opioid receptors contributed to the antinociception of each analog. These include compounds where mu opioid receptors (MOR) are not involved (3607 and 3609), and compounds were kappa opioid receptors (KOR) are not involved (3613). In contrast to the parent peptides (i.e., 2801 and 2802), only one of the analogs exhibited KOR antagonism in vivo. Only one stereoisomer, 3605, exhibits KOR antagonist activity, but the dose-response of the antagonism of this compound is unusual. Three of the stereoisomers, 3605, 3608, and 3613, exhibit DOR antagonist activity. In interesting comparison to the other cyclic tetrapeptides, compound 3613 (DDDD) is a mu opioid receptor (MOR) agonist and delta opioid receptor (DOR) antagonist. MOR agonists/DOR antagonists are of great interest because of their decreased liability profile (decreased addiction potential and liability profile such as tolerance) compared to MOR agonists like morphine. In addition, compound 3613 is effective in preventing stress-induced reinstatement of cocaine seeking behavior in the conditioned place preference assay (FIG. 5). This is a surprising result given that compound 3613 does not appear to to have KOR antagonist activity.

Referring now to FIGS. 1-3B, data from various assays show that compounds 3605, 3607, and 3708 show activity against pain in a number of models. These models are based on the formalin assay, the acetic acid stretching assay, and the nerve constriction assay. The formalin and acetic acid stretching assays are indicative of activity against inflammatory pain (i.e., nociceptive pain) and the nerve constriction assay is indicative of activity against neuropathic pain.

Inflammatory pain (i.e., nociceptive pain) is caused by stimulation of peripheral nerve fibers that respond only to stimuli approaching or exceeding harmful intensity (nociceptors), and may be classified according to the mode of noxious stimulation. The most common categories being "thermal" (e.g., heat or cold), "mechanical" (e.g., crushing, tearing, shearing, etc.) and "chemical" (e.g., salt or iodine in a cut).

Neuropathic pain is caused by damage or disease affecting any part of the nervous system involved in bodily feelings (the somatosensory system). Peripheral neuropathic pain is often described as "burning", "tingling", "electrical", "stabbing", or "pins and needles".

Figure 1:
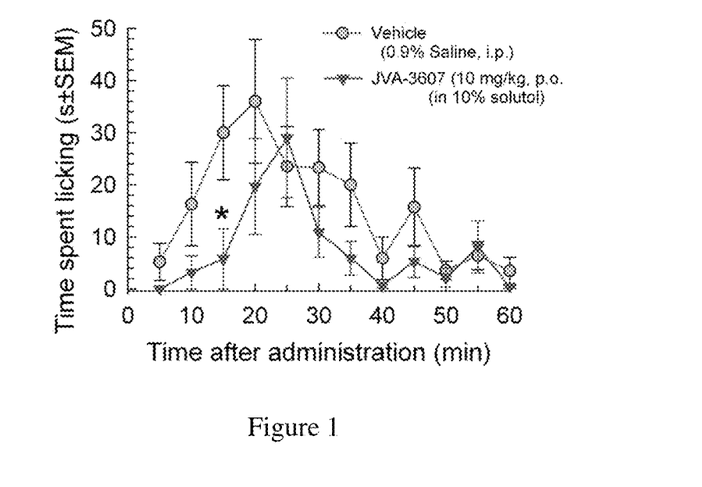
FIG. 1 illustrates an analgesic effect of a cyclic tetrapeptide in a formalin assay.

FIG. 1 demonstrates that a 10 mg/kg oral administration of 3607 is effective in alleviating pain in the formalin assay as compared to intraperitoneal administration of saline. It entails the injection of a dilute solution of formalin into the surface of the rodent's hindpaw, followed by the scoring of stereotypical behaviors such as flinching, licking, and biting of the affected hindpaw. The behaviors last for approximately 1 hour, with the early or acute stage (directly after injection) reflecting direct activation of nociceptors and the late or tonic phase (15 to 20 minutes after the injection) reflecting inflammation. Administration of 3607 produced a significant reduction in the time spent licking after formalin administration.

Figure 2:
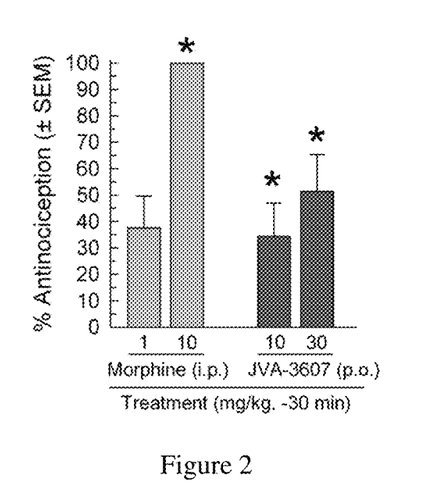
FIG. 2 illustrates an analgesic effect of a cyclic tetrapeptide in an acetic acid stretching assay.

FIG. 2 demonstrates that administration of 3607 was effective for pain reduction in the acetic acid stretching assay. The acetic acid stretching assay is a model for visceral pain and is the most popular chemical assay of nociception. In the assay, subjects are given a subcutaneous (s.c.) injection of drug or vehicle 60 min before an intraperitoneal (i.p.) injection of 0.6% acetic acid. After administration of the acetic acid, the subjects are placed in clear cages (11×7×5 in) and scored for abdominal stretches during a 20 min observation period. Stretching was defined as body contortions, belly pressing, and extension of the hind limbs from which visceral nociception was inferred. Administration of 10 mg/kg and 30 mg/kg of 3607 produced significant antinociception as compared to administration of morphine. And while the effect of 3607 was not as pronounced as with morphine, the observed reductions in stretching were significant, indication that 3607 has a significant pain reduction effect.

Figure 3A:
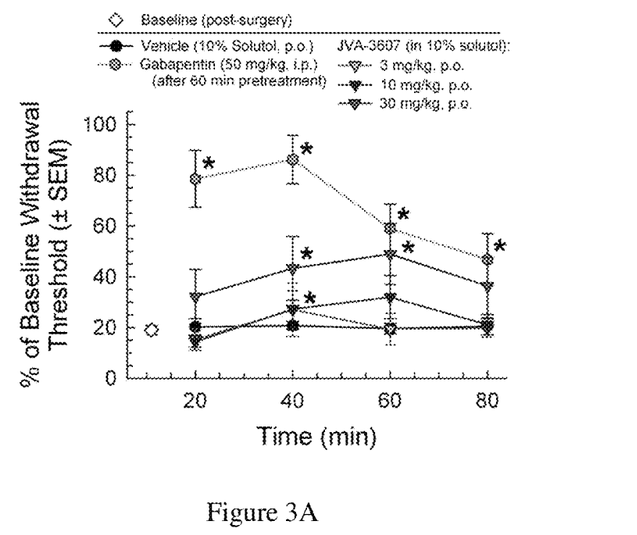
FIG. 3A-3B illustrate an analgesic effect of cyclic tetrapeptides in a nerve constriction assay.
Figure 3B:
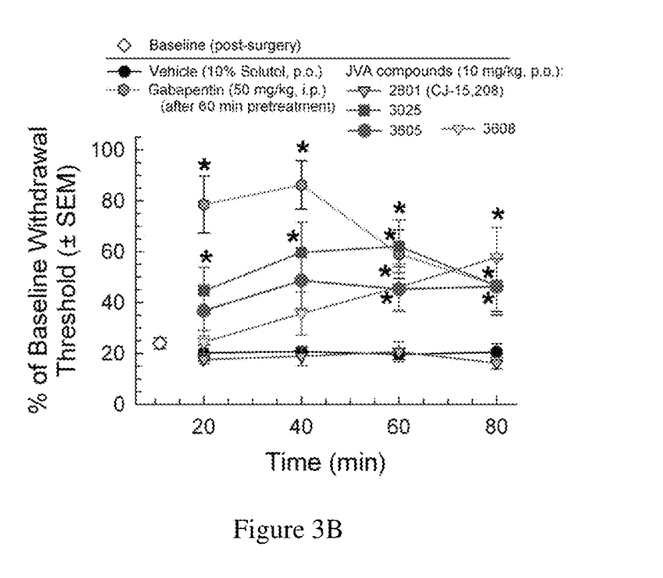
Figure 4:
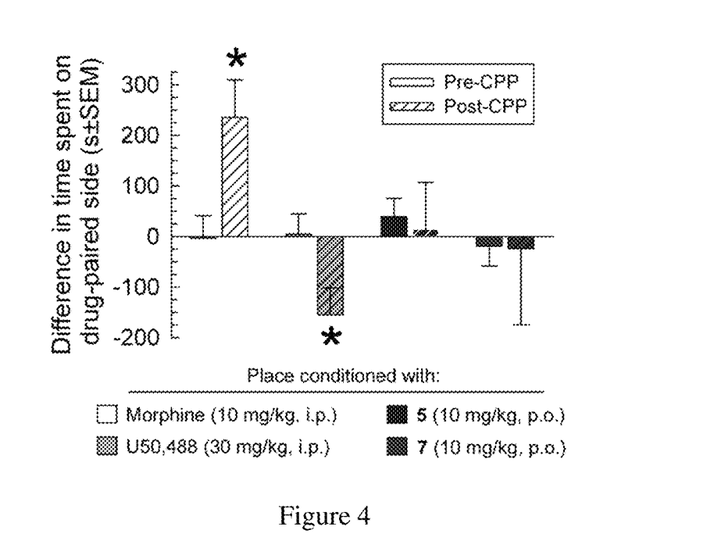
FIG. 4 illustrates that administration of the cyclic tetrapeptides does not induce drug seeking behavior.

Referring now to FIGS. 3A-3B, FIGS. 3A-3B demonstrate that 3607 (FIG. 3A) and 3605 and 3608 (FIG. 3B) are additionally active in the nerve constriction assay for neuropathic pain. In the nerve constriction assay, a nerve of a subject rodent is chronically constricted or cuffed and then the animal is assessed for response to pain stimuli such a paw withdrawal. FIG. 3A demonstrates that 3607 at 3 mg/kg, 10 mg/kg, and 30 mg/kg produces significant relief of neuropathic pain, as compared to 50 mg/kg gabapentin. Gabapentin is an accepted treatment for neuropathic pain. FIG. 3B demonstrates that 3605 and 3608 at 10 mg/kg p.o. produce significant relief of neuropathic pain, as compared to 50 mg/kg i.p. gabapentin and compound 2801.

Interestingly, when screened in an acute tolerance model, the antinociceptive tolerance observed varied markedly among the peptides, from no significant display of tolerance to a rightward shift in the dose-response curve equal to or greater than that exhibited by morphine.

Changes in the macrocyclic tetrapeptide structure were well tolerated with retention of antinociceptive activity, while the KOR antagonism was very sensitive to changes in the aromatic residues. The identification of compounds with potent antinociception that exhibit decreased tolerance in the initial screening is a promising development in the search for potential analgesics with improved liability profiles.

Liability Testing:

TABLE 5

| JVA # | Acute Tolerance $ED_{50}$ shift[a] | Rotorod (10 mg/kg, p.o) | Locomotion (CLAMS, 10 mg/kg, p.o.) | Respiratory depression 10 mg/kg p.o.) |
|---|---|---|---|---|
| 2801 (CJ-15,208) | 1.73 | ✓ (10 and 60 mg/kg) | | |
| 3605 | 19.5-21.5 | ✓ (sig. sedation @ 10 mg/kg, but not 30, mg/kg) | ✓ | Sig. resp. depression |

TABLE 5-continued

| JVA # | Acute Tolerance $ED_{50}$ shift[a] | Rotorod (10 mg/kg, p.o) | Locomotion (CLAMS, 10 mg/kg, p.o.) | Respiratory depression 10 mg/kg p.o.) |
|---|---|---|---|---|
| 3606 | Substantial shift[c] | ✓ | Sig. hypo-locomotion | ✓ |
| 3607 | 5.19 | ✓ | ✓ | ✓ |
| 2802 ([D-Trp]CJ-15,208) | | | (60 mg/kg) | |
| 3609 | 1.87 | ✓ (sig sedation at 40-60 min only) | Sig. hypo-locomotion | Resp. depression |
| 3608 | 9.87 | ✓ | Sig. hypo-locomotion | Resp. depression |
| 3613 | 2.55 | ✓ | ✓ | ✓ |

[a]Morphine sulfate causes 9.2 fold shift in the $ED_{50}$ under these conditions;
[b] ✓ indicates tested (if no other comment then no significant effect);
[c]Cannot reliably calculate $ED_{50}$ values because compound is a partial agonist.

As shown in Table 5, the tested compounds performed generally well in liability testing assays. In acute tolerance assays, the shift in the $ED_{50}$ values varied markedly from minimal (3609 and 3613) to more than morphine (3605). This was surprising. In a rotorod test for sedation and motor coordination, only in the case of 3605 were effects similar to the KOR selective agonist U50,488, suggesting sedation.

None of the compounds showed hyperlocomotion like morphine and other MOR agonists. Given that most of the analogs did not show evidence of sedation in the rotorod assay, the decreases in locomotion observed are probably not due to sedation. Some analogs, namely 3605, 3608, and 3609, did show evidence of respiratory depression at 10 mg/kg, p.o.

Based on the liability profiles the most promising stereoisomers appear to be 3607 and 3613.

Referring now to FIG. 4, it was observed that compounds 3605 and 3607 do not show evidence of conditioned place preference (drug seeking behavior) or conditioned place aversion following oral administration. Compounds 3605 and 3607 were compared to morphine and U50,488, which show significant conditioned place preference (drug seeking behavior) and conditioned place aversion, respectively.

L-Proline Containing Peptides:

In vitro results: These stereoisomers show low affinity for KOR ($K_i > 1$ μM).

They also generally show low affinity for MOR, with only two stereoisomers exhibiting a $K_i < 1$ μM. These compounds exhibit negligible affinity for DOR In Vivo Results:

To date most of these stereoisomers have only been evaluated following i.c.v. administration. Only selected analogs have been evaluated at doses >10 nmol.

Stereoisomers With Demonstrated Antinociceptive Activity:

3612: $ED_{50}$=3.52 (2.01-6.42) nmol i.c.v., 4.28 (3.56-5.27) mg/kg p.o. (KOR, MOR and DOR involved)
3638: $ED_{50}$=8.93 (1.96-19.5) nmol i.c.v.
3639: $ED_{50}$=49.7 (34.8-69.8) nmol i.c.v.

No or only weak antagonist activity has been detected for these stereoisomers to date, but some analogs have only been tested at a lower dose (10 nmol i.c.v.)

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference in their entirety.

What is claimed is:

1. A method for treating and/or preventing depression or depression and anxiety, comprising administering to a subject a therapeutically effective amount of a pharmaceutical composition comprising:

a therapeutically effective amount of a cyclic tetrapeptide comprising a structure of Formula 1 with an amino acid sequence of cyclo[Phe-Pro-Phe-Trp] (SEQ ID NO: 1), or a derivative thereof, wherein the cyclic tetrapeptide comprises an amino acid configuration selected from the group consisting of [LDDL], [DDLL], [DDDL], [DDLD], [LLLL], [LLDL], [DLLL], [DLDL], [LLLD], [LLDD], [DLDD], and [DLLD], and wherein the amino acid configuration of the cyclic tetrapeptide does not comprise [LDLL]; and Formula 1 a pharmaceutically acceptable excipient or carrier.

2. The method of claim 1, wherein the amino acid configuration of the cyclic tetrapeptide is selected from the group consisting of [DDLL], [DDDL], and [DDLD].

3. The method of claim 1, wherein the amino acid configuration of the cyclic tetrapeptide is selected from the group consisting of [DDLL] and [DDDL].

4. The method of claim 1, wherein the amino acid configuration of the cyclic tetrapeptide is [DDDL].

5. The method of claim 1, wherein the therapeutically effective amount of the cyclic tetrapeptide is effective for depression.

6. A method for treating and/or preventing depression, comprising administering to a subject a therapeutically effective amount of a pharmaceutical composition comprising:

a therapeutically effective amount of a cyclic tetrapeptide comprising a structure of Formula 1 with an amino acid sequence of cyclo[Phe-Pro-Phe-Trp] (SEQ ID NO: 1), or a derivative thereof, wherein the cyclic tetrapeptide comprises an amino acid configuration selected from the group consisting of [LDDL], [DDLL], [DDDL], [DDLD], [LLLL], [LLDL], [DLLL], [DLDL], [LLLD], [LLDD], [DLDD], and [DLLD], and wherein the amino acid configuration of the cyclic tetrapeptide does not comprise [LDLL]; and Formula 1 a pharmaceutically acceptable excipient or carrier.

7. The method of claim 6, wherein the amino acid configuration of the cyclic tetrapeptide is selected from the group consisting of [DDLL], [DDDL], and [DDLD].

8. The method of claim 6, wherein the amino acid configuration of the cyclic tetrapeptide is selected from the group consisting of [DDLL] and [DDDL].

9. The method of claim 6, wherein the amino acid configuration of the cyclic tetrapeptide is [DDDL].

10. The method of claim 6, wherein the therapeutically effective amount of the cyclic tetrapeptide is effective for depression.

11. A method for treating and/or preventing anxiety, comprising administering to a subject a therapeutically effective amount of a pharmaceutical composition comprising:

a therapeutically effective amount of a cyclic tetrapeptide comprising a structure of Formula 1 with an amino acid sequence of cyclo[Phe-Pro-Phe-Trp] (SEQ ID NO: 1), or a derivative thereof, wherein the cyclic tetrapeptide comprises an amino acid configuration selected from the group consisting of [LDDL], [DDLL], [DDDL], [DDLD], [LLLL], [LLDL], [DLLL], [DLDL], [LLLD], [LLDD], [DLDD], and [DLLD], and wherein amino acid configuration of the cyclic tetrapeptide does not comprise [LDLL]; and Formula 1 a pharmaceutically acceptable excipient or carrier.

12. The method of claim 11, wherein the amino acid configuration of the cyclic tetrapeptide is selected from the group consisting of [DDLL], [DDDL], and [DDLD].

13. The method of claim 11, wherein the amino acid configuration of the cyclic tetrapeptide is selected from the group consisting of [DDLL] and [DDDL].

14. The method of claim 11, wherein the amino acid configuration of the cyclic tetrapeptide is [DDDL].

15. The method of claim 11, wherein the therapeutically effective amount of the cyclic tetrapeptide is effective for anxiety.

* * * * *